(12) United States Patent
O'Dell et al.

(10) Patent No.: US 7,733,084 B1
(45) Date of Patent: Jun. 8, 2010

(54) EDDY CURRENT ACQUISITION SYSTEM

(76) Inventors: Tom O'Dell, 2125 Squak Mt. Loop SW., Issaquah, WA (US) 98027; Florian Hardy, 121 rue des Lavandieres, St.-Augustin, Quebec (CA) G3A 2R4

( * ) Notice: Subject to any disclaimer, the term of this patent is extended or adjusted under 35 U.S.C. 154(b) by 823 days.

(21) Appl. No.: 11/458,448

(22) Filed: Jul. 19, 2006

(51) Int. Cl.
  *G01N 27/72* (2006.01)
  *G01N 27/90* (2006.01)
(52) U.S. Cl. ......................... 324/220; 702/38
(58) Field of Classification Search ......... 324/219–220, 324/228, 232, 234–235, 238–243; 702/38
  See application file for complete search history.

(56) References Cited

U.S. PATENT DOCUMENTS

| | | | | |
|---|---|---|---|---|
| 4,942,545 A | * | 7/1990 | Sapia | 702/97 |
| 5,174,165 A | * | 12/1992 | Pirl | 73/866.5 |
| 5,329,230 A | * | 7/1994 | Viertl et al. | 324/262 |
| 6,606,920 B2 | * | 8/2003 | Hawkins et al. | 73/866.5 |
| 6,877,389 B2 | * | 4/2005 | Lewis et al. | 73/866.5 |

* cited by examiner

*Primary Examiner*—Bot L LeDynh
(74) *Attorney, Agent, or Firm*—David L. Tingey

(57) ABSTRACT

An eddy current acquisition system integrates traditional elements of a nuclear steam generator tubing inspection into a single modular system comprising three subsystems: the take-up reel subsystem, the acquisition instrument, which is located in the hub of the take-up reel, and the pusher head subsystem. All of the control electronics are respectively enclosed in bases of the pusher head and the take-up reel subsystems in water-resistant and dust proof enclosures. Simplified setup is achieved by employing a single communication bus linking an identification ("ID") chip in each component to a host computer. The ID chip stores and reports product part numbers, descriptions and serial numbers and revision or upgrade status and may also store statistical information such as device duty cycles, performance statistics, repair history, and the like. It also enables auto-fill of product information into firmware of the acquisition instrument, including probe pusher ID, take-up reel module ID, eddy current instrument ID, probe product ID and their serial numbers. It also provides automated inventory management by updating the probe inventory database based when probes are attached and detached from the system. Also implemented in the acquisition instrument module is a real-time landmark detection firmware system.

23 Claims, 7 Drawing Sheets

EDDY CURRENT ACQUISITION SYSTEM

BACKGROUND

Eddy current acquisition systems typically comprise an acquisition instrument, a probe cable slip ring, a probe, a probe adapter, a probe pusher, a take up reel, a probe pusher power supply, a probe pusher controller and in the case of inspection techniques requiring rotating probe technologies, a probe motor controller. For different test missions compatible components must be assembled into an inspection system particular to the mission. A probe is selected for an inspection technique and may incorporate an eddy current bobbin, rotating coil technologies or array probe technologies. A probe adapter compatible with the probe, probe extension cable and the acquisition instrument is also collected. The probe coils, via wires running through the probe shaft, are connected to an acquisition instrument via the probe adapter probe extension cable and the probe cable slip ring. In the case of a rotating probe, probe motor control wires are also routed through the probe shaft and connected to a suitable probe motor controller. The probe pusher that urges the probe on its distal end through a target is connected to a compatible probe pusher controller and probe pusher power supply by controller and power supply cables specific to the hardware.

Routinely, a variety of each component is required to assemble required components for a given mission, and the assembled components need to be correctly configured, both through hardware and software, for each mission. Avoiding human error in assembling the components and correctly configuring them is time-consuming and imperfect, resulting in a costly loss of measurement time and data and a risk of damage to the components, but perhaps most costly is the human exposure to radiation required to assemble and configure these several components into an efficacious eddy current test system.

The objective of the present invention is to present components of an eddy current test system in a consolidated footprint and each with an identifier and each connected to a host computer that recognizes each element and confirms that the components are appropriate to a mission type. The computer also recognizes compatible and incompatible components for the mission and confirms compatibility to the user or directs the user to a change of components.

It is characteristic in eddy current measurement of remote tubular targets that the eddy current probe is pushed through the target by the probe pusher to a target measurement position previously located as a zone of interest for inspection in the target. The probe is advanced to the known position by tracking linear movement of the shaft through the probe pusher a predetermined distance. Typically, the shaft probe pusher includes an encoder that tracks probe shaft movement. However, there is mechanical error measuring distance as a length of shaft pushed through the probe pusher caused by shaft sag, pusher wheel slippage and also from substitution of different probe pushers, shafts, and take-up reels employed for different measurements. Therefore, it is another object to provide a measurement that repeatably and reliably locates a probe at a position within the target that is not dependent on the particular system components assembled.

To maintain the probe shaft taut between the probe pusher and the take-up reel it is usual to employ a mechanical clutch on the reel. Mechanical clutches are effective but present a maintenance and adjustment challenge. Because the pusher and reel are contaminated after use, repair or adjustment are usually done in a "hot shop" environment where radiation protection is required. Repair is cumbersome and expensive, so by eliminating known maintenance issues such as the mechanical clutch, associated operating costs can be reduced. It is therefore a further object to provide an electronic clutch that does not require the maintenance and adjustment of a mechanical clutch.

SUMMARY

These objects are achieved in Zetec's MIZ®-80/D, an eddy current acquisition system that integrates the traditional elements of a nuclear steam generator tubing inspection into a single modular system comprising three subsystems: the take-up reel subsystem, the acquisition instrument, which is located in the hub of the take-up reel, and the pusher head subsystem. All of the control electronics are respectively enclosed in bases of the pusher head and the take-up reel subsystems in water-resistant and dust proof enclosures. By integrating these subsystems into one modular system, the user has fewer system modules to carry into containment and fewer electrical cable connections to make. This architecture reduces the number of cables required from thirteen in previous eddy current test systems to three in the present system. This results in much faster set-up, improved system reliability, and simplified troubleshooting. More efficient set-up reduces human radiation exposure and reduces inspection labor costs.

Simplified setup is further achieved by the MIZ-80/D technology employing a single communication bus linking an identification ("ID") chip in each component to a host computer (1-Wire® technology from Maxim/Dallas). The ID chip stores and reports product part numbers, descriptions and serial numbers and revision or upgrade status. The 1-Wire® chip may also store statistical information such as device duty cycles, performance statistics, repair history, and the like. It also enables auto-fill of product information into software of the acquisition instrument, including probe pusher ID, take-up reel module ID, eddy current instrument ID, probe product ID and their serial numbers. It also provides automated inventory management by updating the probe inventory database based when probes are attached and detached from the system.

The communication bus and ID chip typically employ the MIZ-iD EEPROM device identification technology commercially available from Dallas-Maxim semiconductor, which provides the foundation for system level setup and configuration efficiencies, setup validation and inspection error-proofing. Each ID chip is programmed at the time of manufacture with unique data format known only to the MIZ®-iD system. Each system component is automatically logged into a host computer by the MIZ-iD link and compared against mission requirements and component compatibility and against a probe inventory management database and the selected inspection, confirming system viability to the operator or warning the operator of component incompatibilities and even disabling the system until appropriate compatibility corrections are made. In so doing, accidental recording of impertinent data due to configuration or hardware mismatch or damage to system components is prevented.

Another advantage gained by use of MIZ-iD in each system component and particularly in the probe is automatic configuration of a multiplexer switch on a probe interface module in accordance with the probe type. Without MIZ-iD a user must select the appropriate adapter cable to physically adapt the standard connector on an instrument to the specific pin-out on the probe being used. If an incorrect adapter is used, incorrect voltage levels could be applied to pins that could cause damage to the probe or the instrument. Instead, employing MIZ-iD, the computer compares the probe type and the currently loaded eddy current acquisition technique, and, if the components are compatible and suitable for the mission, dynamically configures the multiplexer switch on the probe interface module to match the probe. This eliminates a need for a wide range of adapter cables and prevents damage associated with a probe through adapter cable mismatch.

The eddy current test system employs an acquisition instrument module in the hub of the take-up reel. Analog eddy current drive frequencies and returned frequency response signals are communicated through the probe to the acquisition instrument module, which is mounted within the reel hub, and processed at the instrument module into digital data to be transmitted to the host computer software. Only digital signals are transmitted from the instrument module to the host computer through a slip ring on the hub. Early data processing and conversion to a digital signal before passing through the slip ring reduces data sensitivity to noise. Transmission of only digital signals through the slip ring also increases tolerance for slip ring contact impedance changes as a function of contact wear over the life of the slip ring. This results in improved signal-to-noise ratios, more robust eddy current data and lower maintenance costs in the form of longer life slip rings.

Also implemented in the acquisition instrument module is a real-time landmark detection firmware system. Steam generator tubes are typically supported by a tube sheet and several tube supports and anti-vibration bars mounted at known intervals along the tube runs. These supports and anti-vibration bars prevent tubes from vibrating and migrating from their fixed positions under pressure and temperature. They also change the magnetic field and influence the eddy current signature of the tubing as a probe is pushed through a tube and passed a support or anti-vibration bar. A similar affect occurs at the end of the tube and at top of the tube sheet. The change in an eddy current signature can be characterized and recognized as a landmark, or a fiduciary reference point of position along the tube using real time data processing of the eddy current signal within the eddy current instrument. The true positions of these locations are known to the system from a landmark table data file (constructed from the steam generator design information). As a landmark signal is detected by a probe and identified by the instrument processing, the system correlates the detected position to the landmark table loaded within the instrument at the beginning of each tube inspection cycle and encoder positional data supplied by the probe pusher encoder that measures distance as length of probe shaft that has passed through the probe pusher. The detected landmark features are thus registered with the site configuration data as fiduciary points to precisely locate the probe in the tube. A difference between the actual probe location and the encoder positional data is applied as a correction to the probe shaft positional data.

Previous systems have attempted landmark detection to provide better probe position accuracy, but the interpretation of the landmark and the resultant motion commands have been done at the host computer resulting in limited success because of data latency. By the time the landmark information reaches the host computer, and depending on the host computer utilization, the opportunity react to an encoder position it may have been missed. In addition, the accuracy of the encoded position of the landmark features compared to the landmark configuration data is compromised by the variables introduced by the probe delivery conduit and the landmark "as built" position dimensions. The problem is circumvented by locating the landmark correlation and encoder position correction process within firmware in the acquisition instrument module and locating that module in the hub of the take-up reel. Thus, dependency on the host computer for positional correction is removed. With accurate probe positional data processed in the acquisition module and probe motion control capability, correction time a response is faster. That is, time required for the computer to direct the probe pusher motor (through the probe pusher controller) to stop or otherwise adjust its progress is reduced, allowing the computer to more accurately position the probe at an zone of interest to be measured without overshooting and missing the acquisition target or undershooting and acquiring data for a larger extent of tubing. Also the probe motor (when present) is activated timely to acquire data at and only at the desired zone of interest to be measured. Additional acquired data equates to additional analysis time, which impacts inspection efficiency and drives costs up.

The electronic clutch comprises a servo motor acting on the take-up reel to bias the take-up reel counter against the more powerful pull of a pusher head motor (and gear train) of the probe pusher. As the pusher head motor spools the probe shaft from the take-up reel either in winding or unwinding, the servo motor provides a light braking force that opposes the pusher head motor. Thus, the shaft remains taut between the take-up reel and the probe pusher.

Efficient testing of steam generator tubes often employs two eddy current probes located in two tubes at the same time. This requires one acquisition system for each probe; that is, a take-up reel module, an acquisition instrument module, a take-up reel control module, a pusher head module, and a pusher head control module pusher is required for each probe. For expediency, these modules are functionally symmetric with the take up reel module provided at each end with a hot shoe connection for receiving the probe pusher module, also with a hot shoe connection at each end. Thus, two sets of like modular components can be employed with one set configured in a "right hand" configuration and another in a "left hand" configuration such that both probe shafts are driven in a same direction. The take up reel module and the probe pusher module are driven in either a clockwise or counter-clockwise rotation. The symmetric spool probe with the probe shaft wound on it is mounted on the acquisition instrument to feed the probe pusher module in the selected left or right hand configuration.

DETAILED DESCRIPTION OF THE PREFERRED EMBODIMENTS

Figure 1:
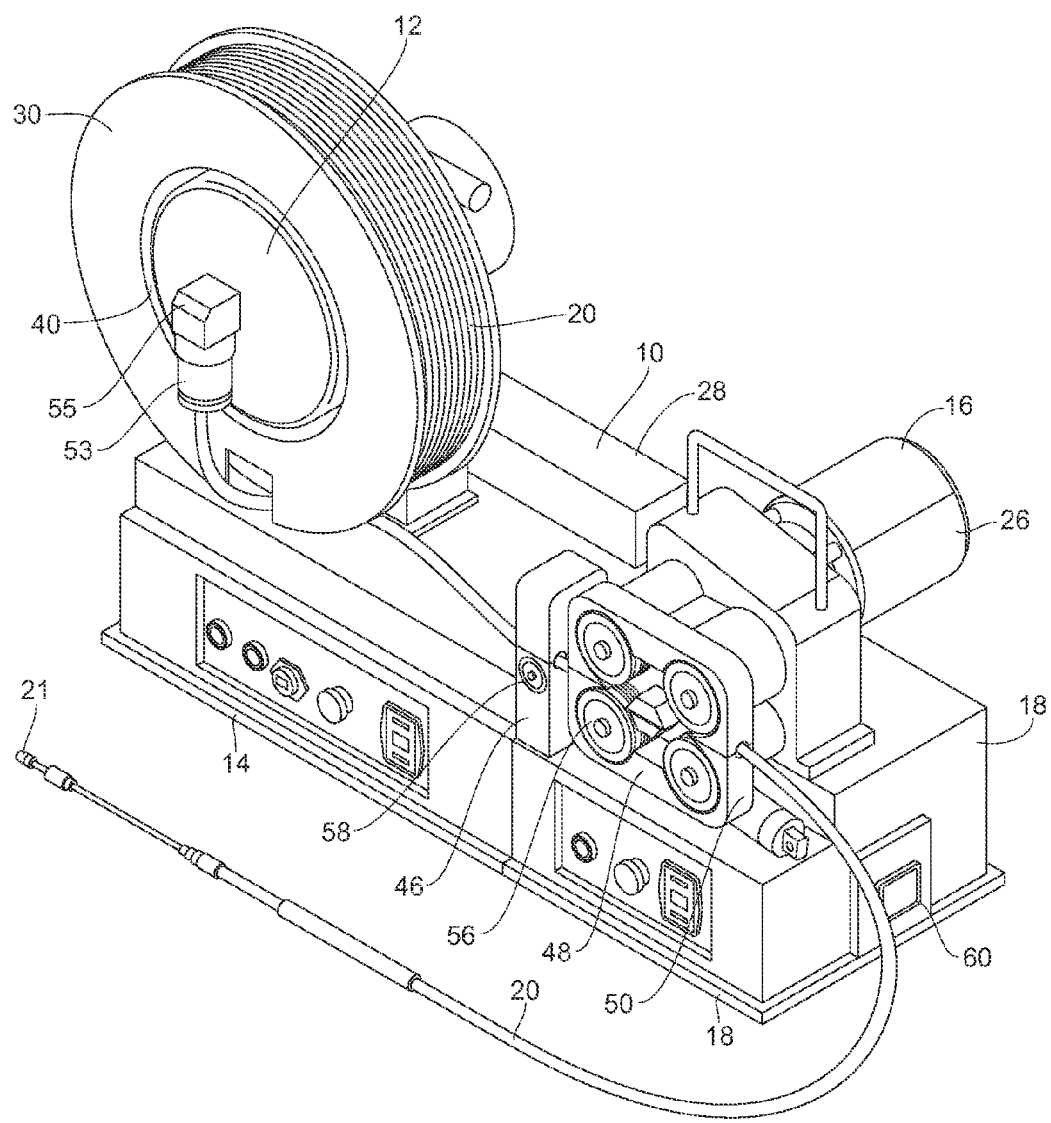
FIG. 1 is a perspective view of the eddy current test system of the present invention.

The eddy current test system of the present invention comprises system components including a take-up reel module 10, an acquisition instrument 12, a take-up reel control module 14, a probe pusher module 16, a probe pusher control module 18, a probe shaft 20 with a probe 21 on its distal end, and a host computer 23. The host computer 23 communicates with each these modules through a primary Ethernet link to the acquisition instrument 12 that provides second level control brokering between host computer 23 and the probe pusher control module 18, take up reel control module 14 and ID network hardware links 22 using serial and 1-Wire® bus communication to the instrument module. All of the above connected components, each with an ID chip 24, report through the acquisition instrument 12 through serial communication to the host computer 23 and are controlled through a single Ethernet data line, including control of motors 26 and 28 of the probe pusher module 16 and the take-up reel module 10 through their respective control modules 14 and 18 and including communication of ID chip data. The ID chip 24 comprises a memory that is configured to receive component information, such as a unique component identifier, the type of device, a device model number, a device serial number, and may include time in operation of the device and calibration dates and other data as appropriate to define the product. Software in the host computer 23 manages ID chip information. The single data line, or 1-Wire, 22 connects to the several ID chips 24 and thus relays component and module data to and from the host computer 23 through the acquisition instrument module 12 via the Ethernet link.

The components containing the ID chip components are an instrument analog board, a probe interface module board, a digital board and the acquisition instrument module 12, a motion control analog board, a motion control digital board, and the take-up reel control module 14, and the probe pusher control module 18. Instrument analog board is an eddy current instrument board that provides the AC sinusoidal drive frequency into the probe coils and differential input amplifiers to receive the frequency response signals from the probe. The MIZ-80iD has a series of drive amplifiers and input amplifiers that create hardware channels of data. The probe interface module board provides the ability to direct the hardware channels of the analog board to specific coils on an eddy current probe by the use of hardware controlled switches depending on the probe configuration. A common 36 pin connector in the probe interface module provides the connection to various probe types supported by the MIZ-80iD. The digital board in the acquisition instrument uses digital circuitry to produce the sinusoidal drive used by the analog board. Multiple drive frequencies can be produced in either multiplexed fashion, simultaneously or both depending on the configuration for the mission. The Digital board also contains the digital circuitry to demodulate the frequency response (U.S. Pat. No. 6,734,669 Digital demodulation of an eddy current signal). The motion control analog board controls and monitors the rotational speed of the rotating probe. It also drives current to the saturation-field probes. The motion control digital board controls and monitors the speed and position of the probe. It does so by monitoring encoders and communicating with servo drives. It also controls solenoids and monitors sense coils that may be part of an eddy current inspection system.

Figure 2:
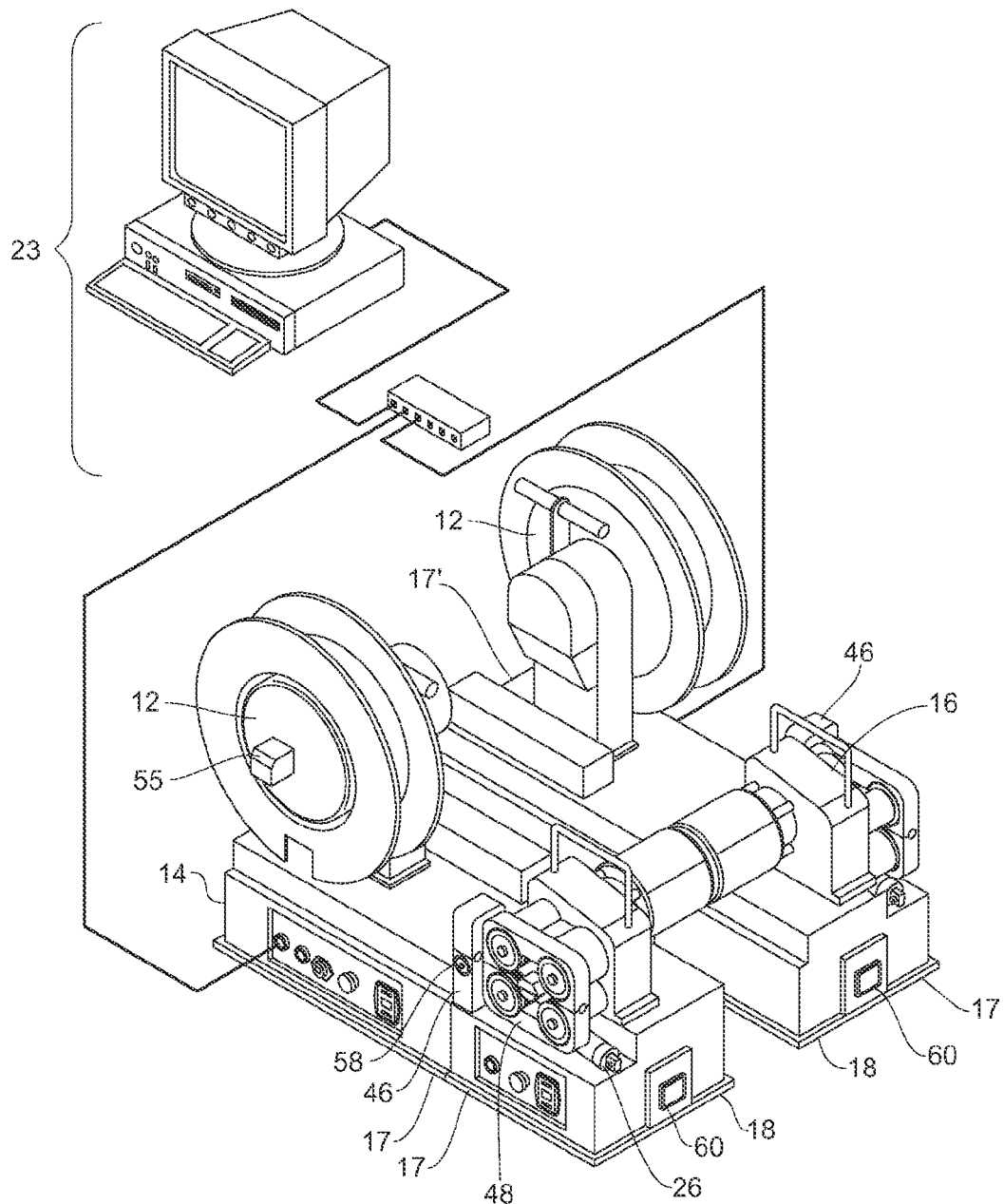
FIG. 2 is a perspective view of two systems of FIG. 1 assembled "back-to-back" and also showing the systems connected to a host computer
Figure 3:
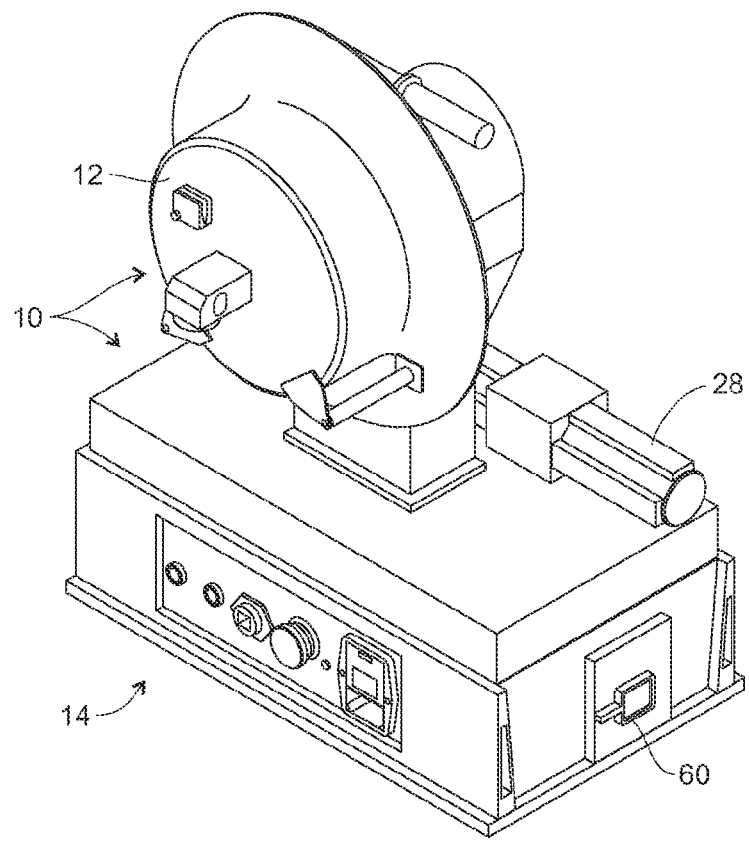
FIG. 3 is a perspective view of the acquisition instrument mounted on the take-up reel module, which is mounted to the take-up reel control module.
Figure 4:
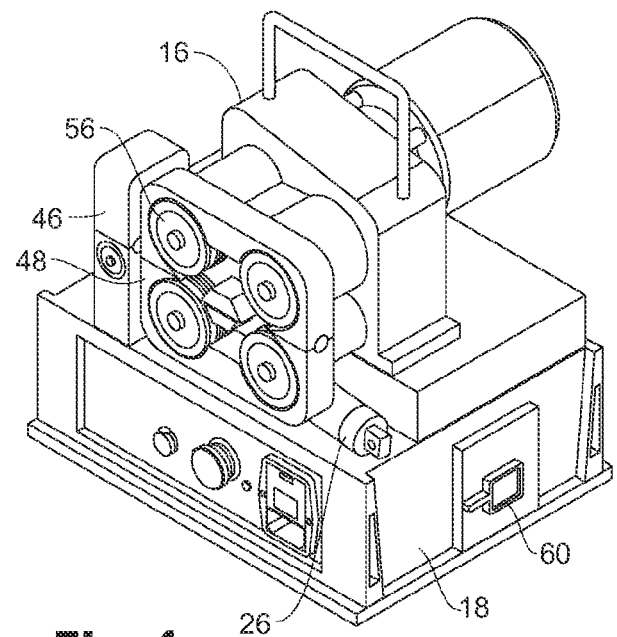
FIG. 4 is a perspective view of the probe pusher module showing probe pusher wheels and an encoder.
Figure 5:
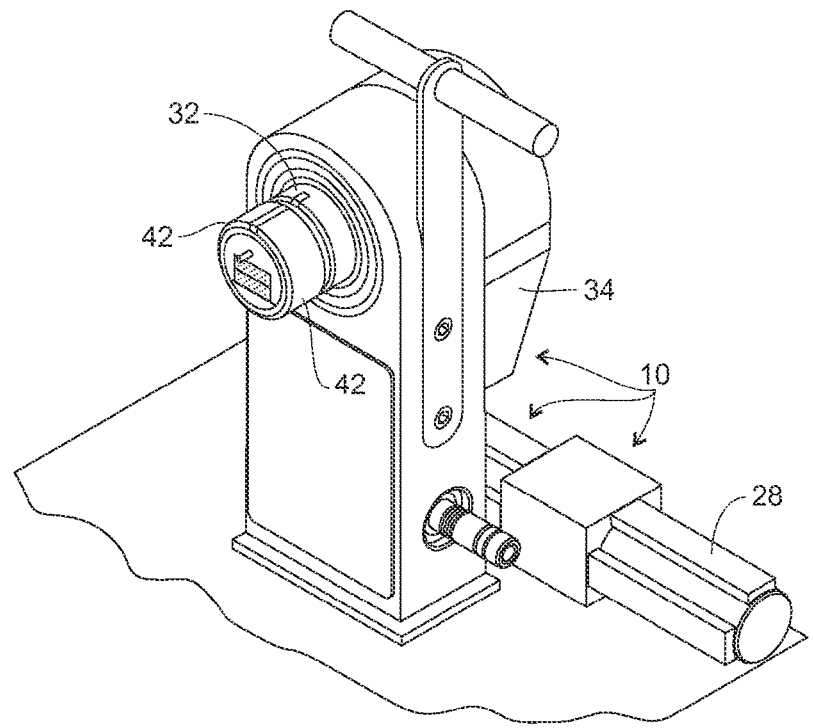
FIG. 5 is a perspective view of the acquisition instrument aligned for mounting on a mount of the take-up reel module.
Figure 6:
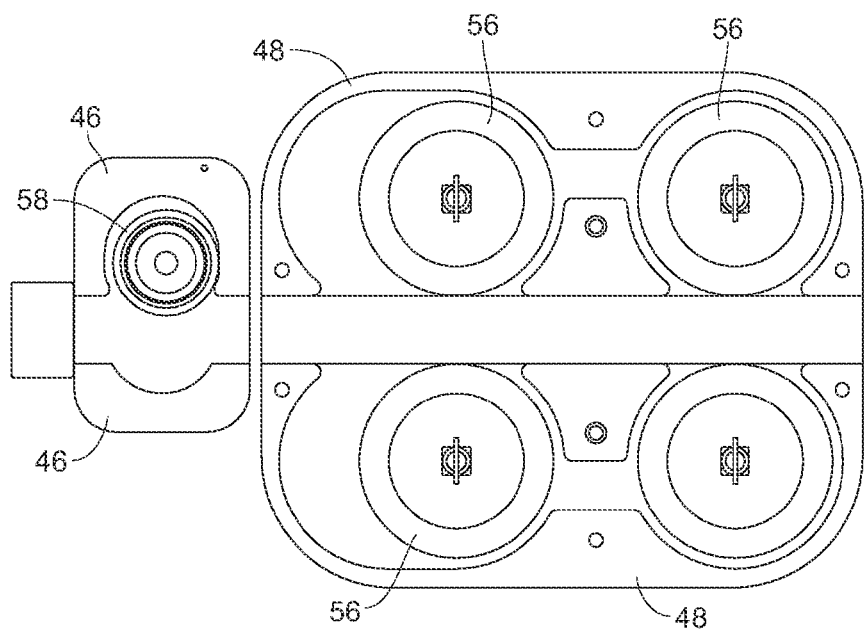
FIG. 6 is an enlarged perspective view of the probe pusher wheels and an encoder
Figure 7:
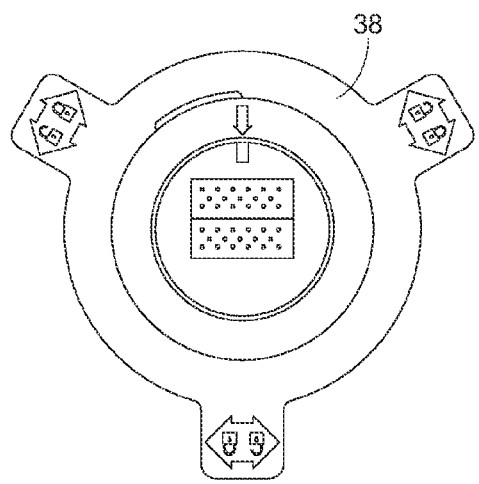
FIG. 7 is a perspective view of the locking mechanism that secures the acquisition instrument to a mount on the take-up reel module, also showing a hot shoe connector for receiving the acquisition instrument.
Figure 8A:
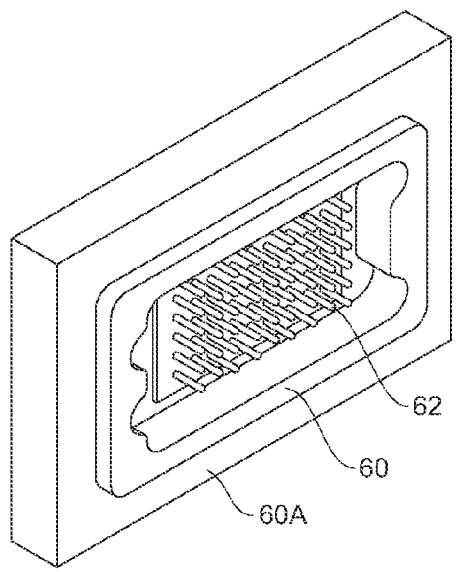
FIG. 8A is a front perspective view of one half a hot shoe connector, showing male pins.
Figure 8B:
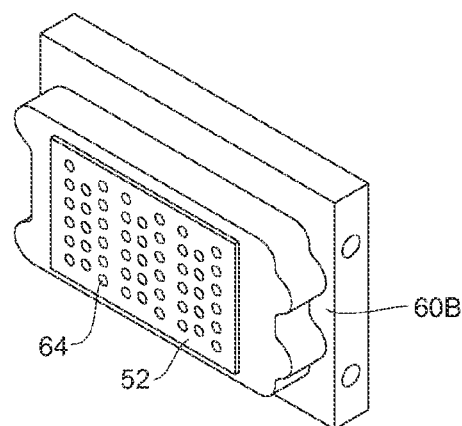
FIG. 8B is a front perspective view of a hot shoe connector a matching half of the hot shoe connector of FIG. 8A, showing female pin holes.
Figure 8C:
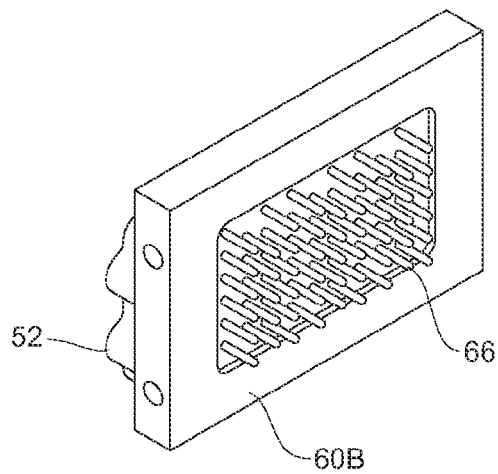
FIG. 8C is a back perspective view of the hot shoe connector half of FIG. 8A showing solder pins.
Figure 8D:
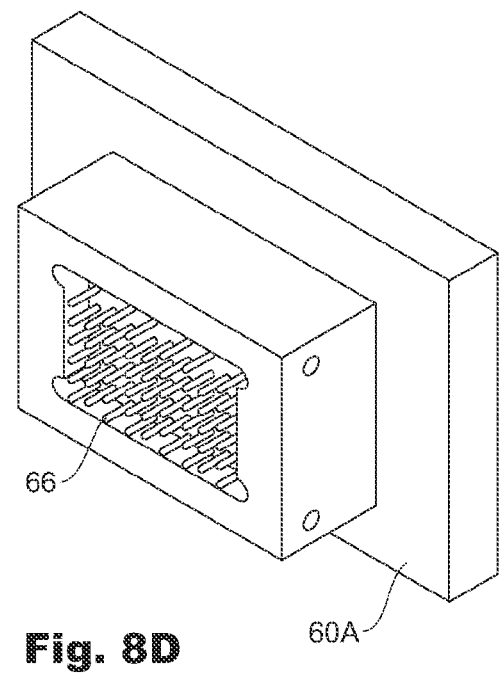
FIG. 8D is a back perspective view of a hot shoe connector half of FIG. 8B, also showing solder pins.
Figure 9:
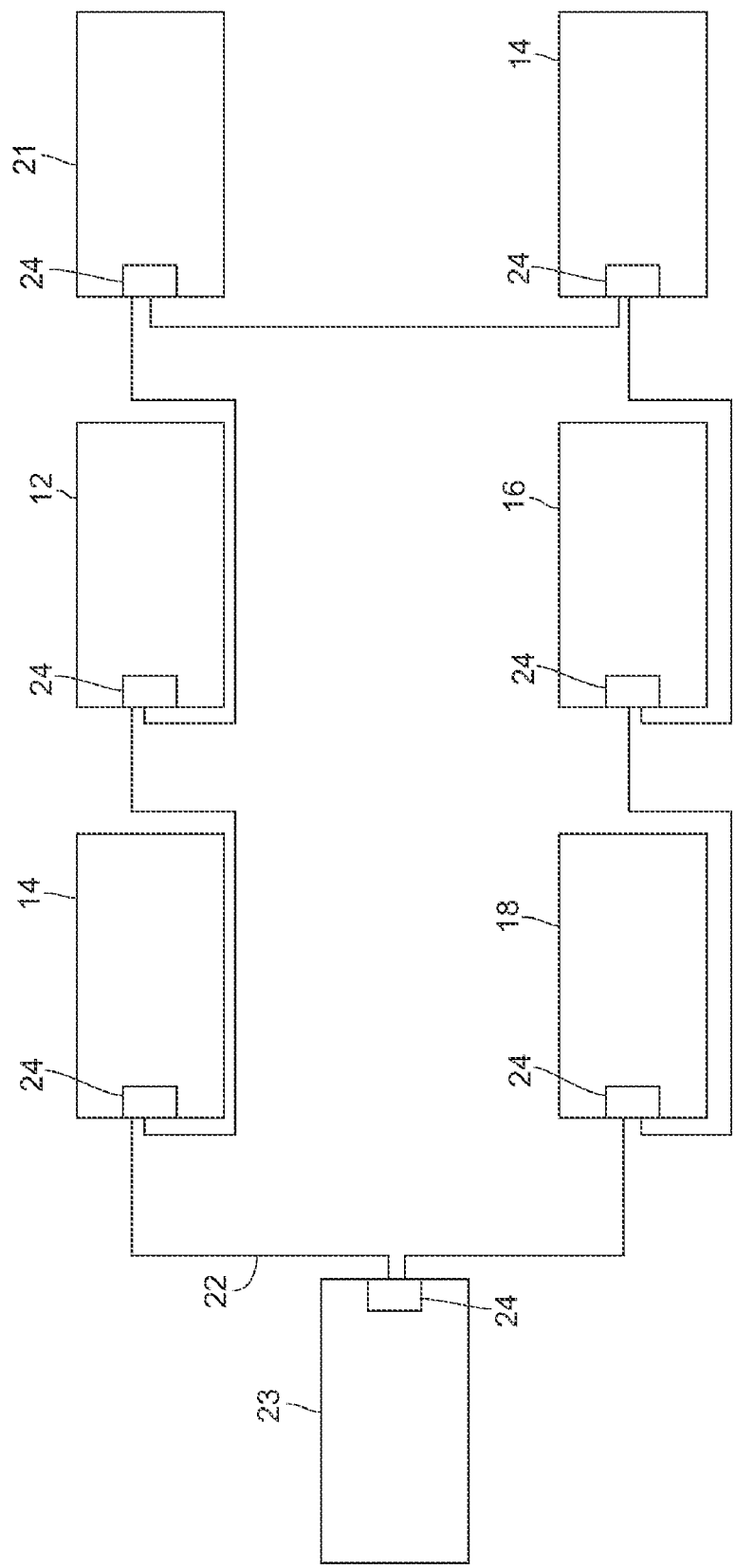
FIG. 9 is a diagram showing interconnection of system modules and components by a 1-Wire connection.

The general layout of the take-up reel module 10 is functionally symmetric so two systems of these same components can be configured "back to back" driving two shafts and probes the same direction as shown in FIG. 2. Functional symmetry is then achieved by rotating each control module so control module ends 17 and 17' not connected in a left hand configuration connect in a right hand configuration. Hot shoe connectors 60 are provided on each of the probe pusher control module 18 and the take-up reel control module 14 ends. The symmetric spool 30 is mounted on the take-up reel motor 28 consistent with a left and a right hand configuration so the shaft unreels toward the probe pusher module 16. The shaft feed 53 is routed from one side of the spool 30 or the other to connect to the acquisition instrument at common 36-pin connector 55. This configuration option allows for one spool 30 to be used in either hand configuration. The take-up reel and probe pusher motors 28 and 26 rotate consistent with the left or right orientation by recognizing which hot shoe connectors 60 of the take-up reel and the probe pusher modules are connected. A control side of the hot shoe connector 60 pulls up a hot shoe connector pin to logic high and another is connected to logic ground. The take-up reel control module 14 uses these signals to determine the direction to drive the take-up reel motor 28 as does the probe pusher control module 18.

Hot shoe connectors 60 the take-up reel control module 14 to the probe pusher control module 18. The hot shoe connector 60 comprises matching halves 60A and 60B with one half 60A comprising male pins 62 and the other half 60B comprising female pin holes 64. Opposite the matching male and female pins 62 and pin holes 64 are solder pins 66 corresponding to the pins 62 and pin holes 64.

The take-up reel control module 10 provides DC power to the acquisition instrument 12, the take-up reel motor 28, which is provided power and control through the motion control analog and digital boards located in the take-up reel module, the probe pusher control module 18, and the 1-Wire 22 and control to the take-up reel module 10. The take-up reel module 10 connects to the pusher control module 14 through hot shoe connectors 60.

The take-up reel module 10 comprises a spool 30 on the acquisition instrument 12, which is mounted on a mount 32 of a drive mechanism 34 that includes a take-up reel motor 28, the probe shaft 20 coiled around the spool 30. A take-up reel encoder (not shown) is located inside the take-up reel motor 26 or otherwise associated with the motion velocity control of the spool 30 compared to the velocity and direction of the probe pusher module drive wheels. Docking connector 38 in the spool hub 40 receives attachment of the acquisition instrument 12 within the spool hub 40. A slip ring 42 is mounted coaxially with the spool 30, the slip ring 42 carrying power and data signals to and from the acquisition instrument 12 to the take-up reel control module 14 below the take-up reel module 10.

The take-up reel control module 14 and the probe pusher control module 18 connect respectively to the respective take-up reel module 10 and the probe pusher module 16 through hot shoe connectors 60 through which data is transferred and electrical power is provided from the respective control modules. The 1-wire 22 from the ID chip 24 in the probe pusher module 16 is routed to the control link 1-Wire controller within the take-up reel control module 14 through which it is read and written.

A take-up reel drive mechanism 44 driving the acquisition instrument 12 within the hub of the spool 30 is controlled by commands to the take-up reel control module 10 from velocity and direction data provided by the probe pusher control section of the motion control board within the take-up reel module. The probe pusher module 16 comprises drive wheels 56 driven by the probe pusher motor 26 to engage and drive the probe shaft 20. The probe pusher module 16 also includes a probe pusher encoder 46 including encoder wheel 58 that rides on the probe shaft 20 and measures probe shaft linear movement through the drive wheels 56 as a rotation of the encoder wheel 58. Thus the encoder wheel 58 is an indicator of probe position as a distance of probe shaft travel from the probe pusher 16. The probe pusher encoder 46 is located between the probe pusher module 16 and the spool 30 where the shaft remains taut to minimize slippage and other read errors by the encoder wheel 58. When the probe pusher module 16 is rotated between right and left orientation, the probe pusher encoder 46 is shifted between mounts on either side of the probe pusher 48 to remain between the spool 30 and the probe pusher 48.

Probe position, or the approximate probe location determined as an encoder count of rotations of the encoder wheel 58 without compensation for slippage and other mechanical inaccuracies, is communicated to the Take-up Reel Control Module 14 by hardware connection and ultimately to the acquisition instrument 12 by way of serial communication. Differences of shaft travel as determined between the drive wheels 56 and the encoder wheel are deemed an indicator of slippage of the drive wheels 56 on the probe shaft 22.

An effective take-up reel electronic clutch is achieved that maintains a tight wrap of the probe shaft 20 onto the spool 30 by employing opposing drive current to the take-up reel motor 28 thus posing a drag resistance to the more powerful probe pusher motor 26 during probe insertion. A similar scheme provides an effective overrun to maintain probe shaft tension on the take-up spool 30 during probe retraction.

The primary function of the acquisition instrument 12 is to drive magnetic flux into the tubes to be inspected and extract acquisition signals utilizing coils from the probe 22 connected to it through the probe shaft 20 and to transmit the signals to the host computer 23. In doing so, it initially receives set-up information from the host computer 23, such as acquisition mission parameters and a map of target landmarks 100, which it uses to calibrate the position of the probe 21 in the target. Based on those parameters and the computed position of the probe 21, it executes an automated sequence for probe inspection of a target zone of interest, including probe data acquisition start and stop.

The programmable host computer 23 is loaded with data acquisition software that receives data acquisition mission parameters and implements a data acquisition sequence in the assembly of system components so the system controls an inspection sequence by itself. The host computer 23 receives an inspection plan for the next target to inspect with mission parameters such as the location of acquisition extents (zones of interest within the target) to inspect, a list of landmarks with their corresponding landmark types and location, the speed of inspection within each respective extent, the direction (push/pull) of the inspection, the speed on push (between extents), eddy current instrument drive parameters such as drive voltages, frequencies, sample rates, channel assignments, probe interface module multiplex parameters, and the speed on pull between extents. Based on the information, the system does the inspection automatically, directing the probe pusher wheels 56 to drive the probe shaft 20 with the probe 21 attached on its distal end to transverse within the target tube while directing the take-up control module 14 to cause the spool 30 to maintain tension on the probe shaft 20 to ensure control of the spooling. The probe 21 is then pushed to an intended location within the target 102. The acquisition instrument 12 then causes the probe 21 to acquire data as the probe 21 is pushed or pulled passed the intended zones of interest.

A portion of the data acquisition software also resides as firmware embedded in the acquisition instrument 12. This firmware comprises instructions for precisely locating the probe 21 as it moves through the target to its intended location without requiring involvement of the host computer 23, including instructions for calibrating the approximate probe location measured by the probe pusher by registering the approximate probe location against locations of known target features detected by the probe 21 as it passes them. The host computer 23 initially sends a list of target features, employed by the system as fiduciary landmarks, to the acquisition instrument 12 where it is loaded into digital memory of the acquisition instrument, including their corresponding type and location. As the acquisition instrument 12 detects landmark target features, the actual probe location is established in the target. The firmware in the acquisition instrument 12 uses landmark table feature location data, signals from the eddy current data channels, mathematical algorithms, and operating frequencies to recognize a landmark feature within the data stream. The firmware in the acquisition instrument 12 compares the actual probe location with the location provided by the probe pusher encoder 46. The probe location as determined by the probe pusher encoder 46 is then adjusted to match locations measured by the acquisition instrument 12. This process repeats at each landmark location, continually updating the accuracy of the position as the probe reach the next target extent where the probe 21 and the acquisition instrument 12 are activated to acquire the desired inspection data.

What is claimed is:

1. An eddy current test system comprising an eddy current probe,
   a host computer, and
   an assembly of selective modules with electrical and data communication between selective modules and the host computer and wherein each module is separable from each other module with each module removable from the assembly of modules and substitutable by a like module for convenience of maintenance and repair, said assembly of modules comprising,
   a take-up reel module selectable from a plurality of optional take-up reel modules further comprising,
      an acquisition instrument selectable from a plurality of optional acquisition instruments,
      a probe shaft selectable from a plurality of optional probe shafts connecting the probe and the acquisition instrument,
      a spool around which the probe shaft is wound and unwound, the acquisition instrument mounted in a spool hub thereby rotating with the spool as the probe shaft is wound and unwound, and
      a take-up reel motor driving the spool,
   a pusher module selectable from a plurality of optional pusher modules aligned with the take-up reel module to receive the probe shaft and further comprising a drive mechanism adapted to engage the probe shaft and push it with the probe attached through a target and withdraw it from the target, a pusher control module selectable from a plurality of optional pusher control modules on which the pusher module releasably mounts and further comprising, a servo drive that provides power and control to a probe pusher motor in the pusher module more powerful than the take-up reel motor, a take-up reel control module selectable from a plurality of optional take-up reel control modules on which the take-up reel module releasably mounts and to which the pusher control module releasably connects, further comprising, a power supply providing electrical power to the acquisition instrument, the take-up reel motor, and the data wire, a drive motor controller controlling the take-up reel motor.

2. The eddy current test system of claim 1 in which at least a portion of eddy current test system components, referred to as recognized components, comprises a unique, electronically-readable component identifier integral with said portion of the components, the components including said modules, eddy current probe, acquisition instrument, and probe shaft, and wherein said data communication comprises mutual data connection between said component identifiers and the host computer.

3. The eddy current test system of claim 2 in which said data communication comprises a single data wire in a loop through at least a portion of said portion of said components and the host computer.

4. The eddy current test system of claim 3 wherein said data wire comprises said data communication.

5. The eddy current test system of claim 2 wherein the host computer comprises a memory including a table of compatible components represented by component identifiers, said components in said table including said modules, eddy current probe, acquisition instrument, and probe shaft, the host computer recognizing connected components and accepting or rejecting them in accordance with criteria in host computer memory provided in cooperation with the table, the host computer providing a display of accepted and/or rejected components.

6. The eddy current test system of claim 2 wherein operational parameters consistent with and particular to said recognized components are downloaded from the host computer to said recognized components.

7. The eddy current test system of claim 6 wherein said acquisition instrument includes a probe adapter automatically configured by said operational parameters.

8. The eddy current test system of claim 1 wherein at least a portion of said modules and acquisition instrument further comprise a hot shoe connection through which they electrically connect, including a data connection and a power connection.

9. The eddy current test system of claim 1 wherein said take-up reel control module is configured to optionally receive connection of the pusher control module at either a first end or at second end opposite the first end, the take-up reel module being functionally symmetric such that the probe shaft operationally feeds from the spool into the probe pusher at either of the take-up reel first or second ends, the take-up reel control module sensing the connection of the pusher control module and as a result directing the take-up reel motor to drive the spool in a direction consistent with feeding and withdrawing the probe shaft through the probe pusher in accordance with the connection of the pusher control module to the take-up reel control module.

10. The eddy current test system of claim 9 further comprising a first take-reel control module with a first take-up reel module mounted thereon connected to a first pusher control module with a first pusher module mounted thereon at a first take-up reel first end, and a second take-reel control module with a second take-up reel module mounted thereon connected to a second pusher control module with a second pusher module mounted thereon at a second take-up reel second end, the first and second pusher modules configured side by side to push or withdraw respective first and second probe shafts in a same direction, first and second take-up reel control modules being of like design and interchangeable, first and second take-up reel modules being of like design and interchangeable, first and second probe pusher control modules being of like design and interchangeable, and first and second probe pusher modules being of like design and interchangeable, therein comprising an assembly of duplicate modules configurable to perform parallel inspections of nearby targets.

11. The eddy current test system of claim 1 wherein the acquisition instrument is mounted in a take-up reel hub, rotating with the spool as the probe shaft is unwound and wound, the acquisition instrument including a programmable processor programmed with data acquisition embedded software to process analog data from the probe and deliver digital data through a take-up reel slip ring on the hub to the host computer.

12. The eddy current test system of claim 11 wherein said data acquisition software includes instructions to receive data acquisition mission parameters from the host computer and implement a data acquisition sequence wherein the spool is caused to turn for unwinding the probe shaft and the probe pusher is caused to engage the probe shaft with the probe attached on its distal end and push the probe to an intended location within the target, the probe then caused to acquire data as the probe is further pushed or pulled past the intended location.

13. The eddy current test system of claim 11 wherein the data acquisition software comprises instructions for precisely locating the probe as it moves through the target to its intended location, including instructions for updating the approximate probe location measured by the probe pusher by registering the approximate probe location against locations of known target features detected as a change in eddy current signal response as the probe passes them and adjusting approximate probe locations to match measured locations, the known target features being previously loaded in memory accessible by the processor.

14. The take-up reel of claim 1 in which the take-up reel motor is directed by the take-up reel control module to rotate at an overrun rate of probe shaft movement during probe withdrawal as compared to the rate of probe shaft movement of the probe pusher motor as directed by the probe pusher control module and a similar under run during probe insertion, therein maintaining a tight wrap of the probe shaft onto the spool.

15. An eddy current test system comprising a probe selectable from a plurality of available probes each having an electrically detectable unique probe identifier, and an acquisition instrument with a configurable probe adapter and having access to a table of compatible probes and operational probe parameters associated with each available probe, the selectable probe being recognized by its probe identifier and accepted or rejected in cooperation with the table and, if accepted, said probe adapter being automatically configured by the acquisition instrument with said operational probe parameters consistent with and particular to said recognized probe.

16. An eddy current test system comprising
an eddy current probe,
a host computer, and
an assembly of selective modules with electrical and data communication between said selective modules and the host computer and wherein at least one of said selective modules is removable from the test system and substitutable by a like module for convenience of maintenance and repair,
in which at least a portion of eddy current test system components, referred to as recognized components, comprises a unique, electronically-readable component identifier integral with said portion of the components, the components including said modules, an eddy current probe, and an acquisition instrument, and wherein said data communication comprises mutual data connection between said component identifiers and the host computer.

17. The eddy current test system of claim 16 wherein said assembly of selective modules further comprises
at least one of (a) said acquisition instrument selectable from a plurality of optional acquisition instruments, (b) a probe shaft selectable from a plurality of optional probe shafts connecting the probe and the acquisition instrument, (c) a spool around which the probe shaft is wound and unwound, the acquisition instrument mounted in a spool hub thereby rotating with the spool as the probe shaft is wound and unwound, (d) a take-up reel module selectable from a plurality of optional take-up reel modules, (e) a take-up reel motor driving the spool, (f) a pusher module selectable from a plurality of optional pusher modules aligned with the take-up reel module to receive the probe shaft and further comprising, (g) a pusher control module selectable from a plurality of optional pusher control modules on which the pusher module releasably mounts, a take-up reel control module selectable from a plurality of optional take-up reel control modules on which the take-up reel module releasably mounts and to which the pusher control module releasably connects.

18. The eddy current test system of claim 16 wherein the host computer comprises a memory including a table of compatible components represented by said component identifiers, said components in said table including said modules, eddy current probes, and acquisition instruments, the host computer recognizing connected components and accepting or rejecting them in accordance with criteria in host computer memory provided in cooperation with the table.

19. The eddy current test system of claim 18 wherein operational parameters consistent with and particular to said recognized components are downloaded from the host computer to the recognized components.

20. The eddy current test system of claim 19 wherein said acquisition instrument includes a probe adapter automatically configured by said operational parameters.

21. An eddy current test system comprising
an eddy current probe,
a host computer, and
an assembly of selective modules with electrical and data communication between said selective modules and the host computer and wherein at least one of said selective modules is removable from the test system and substitutable by a like module for convenience of maintenance and repair,
in which at least a portion of eddy current test system components, referred to as recognized components, comprises a unique, electronically-readable component identifier integral with said portion of the components, the components including said modules, an eddy current probe, and an acquisition instrument, and wherein said data communication comprises mutual data connection between said component identifiers and the host computer.
wherein said components include at least one of an acquisition instrument and a probe shaft, and wherein said data communication comprises mutual data connection between said component identifiers and the host computer,
wherein the host computer comprises a memory including a table of compatible components represented by component identifiers, said components in said table including said modules, eddy current probe, acquisition instrument, and probe shaft, the host computer recognizing connected components and accepting or rejecting them in accordance with criteria in host computer memory provided in cooperation with the table,
wherein operational parameters consistent with and particular to said recognized components are downloaded from the host computer to the recognized components.

22. The eddy current test system of claim 21 wherein said assembly of modules further comprises at least one of (a) said acquisition instrument selectable from a plurality of optional acquisition instruments, (b) a probe shaft selectable from a plurality of optional probe shafts connecting the probe and the acquisition instrument, (c) a spool around which the probe shaft is wound and unwound, the acquisition instrument mounted in a spool hub thereby rotating with the spool as the probe shaft is wound and unwound, (d) a take-up reel module selectable from a plurality of optional take-up reel modules, (e) a take-up reel motor driving the spool, (f) a pusher module selectable from a plurality of optional pusher modules aligned with the take-up reel module to receive the probe shaft and further comprising, (g) a pusher control module selectable from a plurality of optional pusher control modules on which the pusher module releasably mounts, a take-up reel control module selectable from a plurality of optional take-up reel control modules on which the take-up reel module releasably mounts and to which the pusher control module releasably connects.

23. The eddy current test system of claim 21, wherein said acquisition instrument includes a probe adapter automatically configured by said operational parameters.

* * * * *